United States Patent
Sklar

(10) Patent No.: US 11,389,630 B2
(45) Date of Patent: *Jul. 19, 2022

(54) IMPLANTABLE INTRACRANIAL PULSE PRESSURE MODULATOR AND SYSTEM AND METHOD FOR USE OF SAME

(71) Applicant: Frederick H. Sklar, Dallas, TX (US)

(72) Inventor: Frederick H. Sklar, Dallas, TX (US)

(73) Assignee: Frederick H. Sklar, Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/407,999

(22) Filed: Aug. 20, 2021

(65) Prior Publication Data

US 2021/0379345 A1 Dec. 9, 2021

Related U.S. Application Data

(63) Continuation of application No. 16/866,350, filed on May 4, 2020, now Pat. No. 11,103,683.

(Continued)

(51) Int. Cl.
*A61M 27/00* (2006.01)
*A61M 39/24* (2006.01)

(52) U.S. Cl.
CPC .......... *A61M 27/006* (2013.01); *A61M 39/24* (2013.01); *A61M 2039/248* (2013.01);
(Continued)

(58) Field of Classification Search
CPC .. A61M 27/006; A61M 27/002; A61M 27/39; A61M 2039/248; A61M 2202/0464; A61M 2205/3523; A61M 2205/52; A61M 2205/583; A61M 2210/0487; A61M 2230/30

See application file for complete search history.

(56) References Cited

U.S. PATENT DOCUMENTS

| | | | |
|---|---|---|---|
| 3,958,558 A | 5/1976 | Dunphy et al. | |
| 4,014,319 A | 3/1977 | Favre | |

(Continued)

FOREIGN PATENT DOCUMENTS

WO 2018227022 12/2018

*Primary Examiner* — Philip R Wiest
(74) *Attorney, Agent, or Firm* — Scott Griggs; Griggs Bergen LLP

(57) ABSTRACT

An implantable intracranial pulse pressure modulator for treating hydrocephalus in patients of all ages is disclosed as well as a system and method for use of the same. In one embodiment of the implantable intracranial pulse pressure modulator, two one-way valves are interposed in parallel, opposing orientations between a vestibule and a chamber. One of the one-way valves, in response to systole, provides fluid communication from the vestibule to the chamber such that a small aliquot of cerebrospinal fluid (CSF) is displaced from a cerebral ventricle into a ventricular catheter, thereby reducing intraventricular systolic pressure. The other one-way valve, in response to diastole, provides fluid communication from the chamber to the vestibule such that the same volume of CSF is reintroduced into a cerebral ventricle, thereby increasing intraventricular diastolic pressure. Together, both processes work synergistically to reduce intraventricular pulse pressure in order to treat hydrocephalus.

20 Claims, 5 Drawing Sheets

Related U.S. Application Data

(60) Provisional application No. 62/972,617, filed on Feb. 10, 2020.

(52) U.S. Cl.
CPC ............... *A61M 2202/0464* (2013.01); *A61M 2205/3523* (2013.01); *A61M 2205/52* (2013.01); *A61M 2205/583* (2013.01); *A61M 2210/0687* (2013.01); *A61M 2230/30* (2013.01)

(56) References Cited

U.S. PATENT DOCUMENTS

| | | | |
|---|---|---|---|
| 4,281,667 A | 8/1981 | Cosman | |
| 5,326,374 A | 7/1994 | Ilbawi et al. | |
| 7,510,533 B2 | 3/2009 | Mauge et al. | |
| 7,949,394 B2 | 5/2011 | Salo et al. | |
| 8,292,856 B2 * | 10/2012 | Bertrand ................. | A61M 1/74 604/317 |
| 9,033,909 B2 * | 5/2015 | Aihara ................. | A61M 27/006 604/9 |
| 9,717,890 B2 | 8/2017 | Holper et al. | |
| 9,925,360 B2 * | 3/2018 | Ludin ................. | A61M 27/006 |
| 2008/0139959 A1 | 6/2008 | Miethke et al. | |
| 2009/0204019 A1 | 8/2009 | Ginggen et al. | |
| 2009/0287084 A1 * | 11/2009 | Ragauskas ............... | A61B 8/06 600/454 |
| 2011/0066072 A1 | 3/2011 | Kawoos et al. | |
| 2012/0226215 A1 * | 9/2012 | Hsu .................... | A61M 27/006 604/9 |
| 2020/0061355 A1 * | 2/2020 | Barnea ................. | A61B 5/6853 |

\* cited by examiner

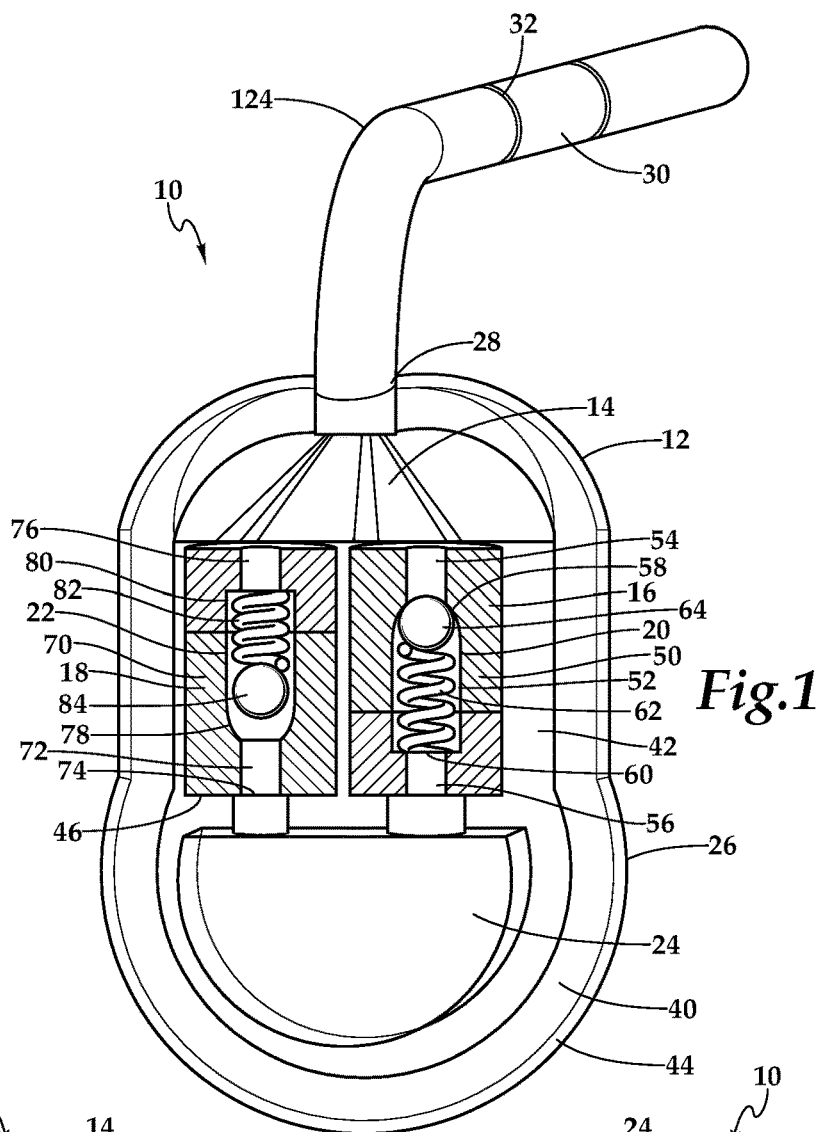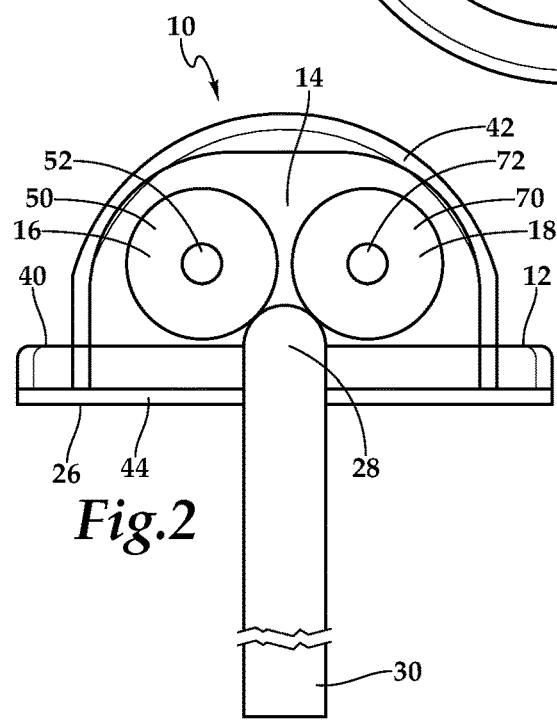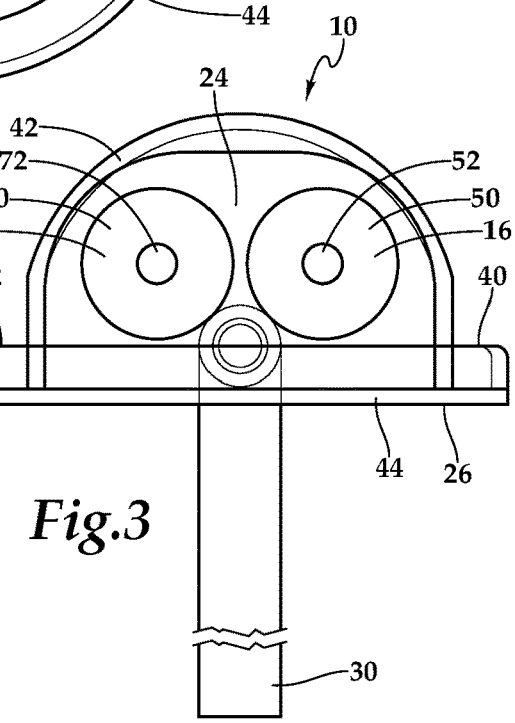

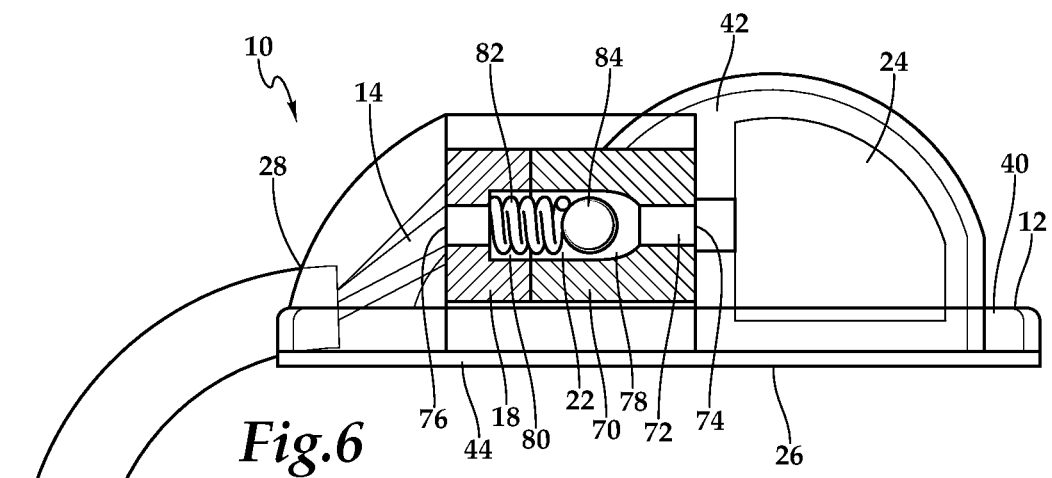
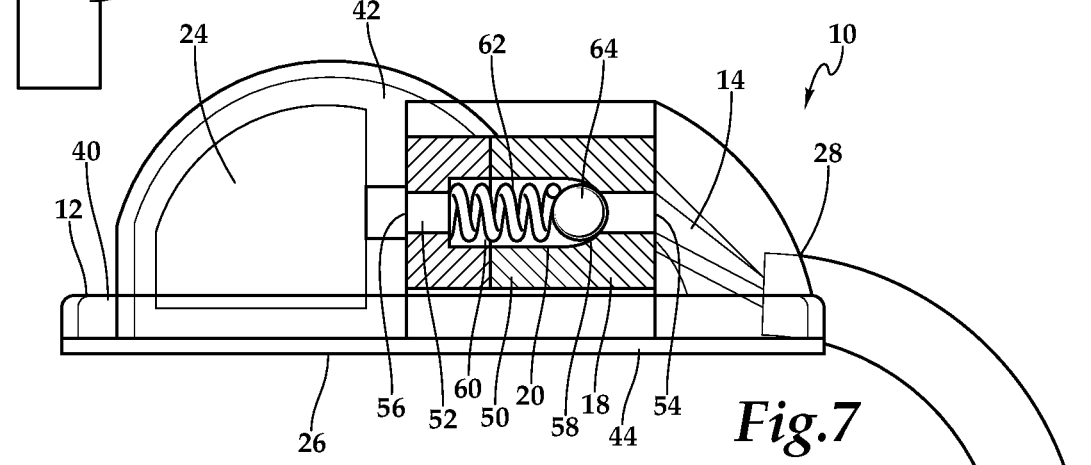
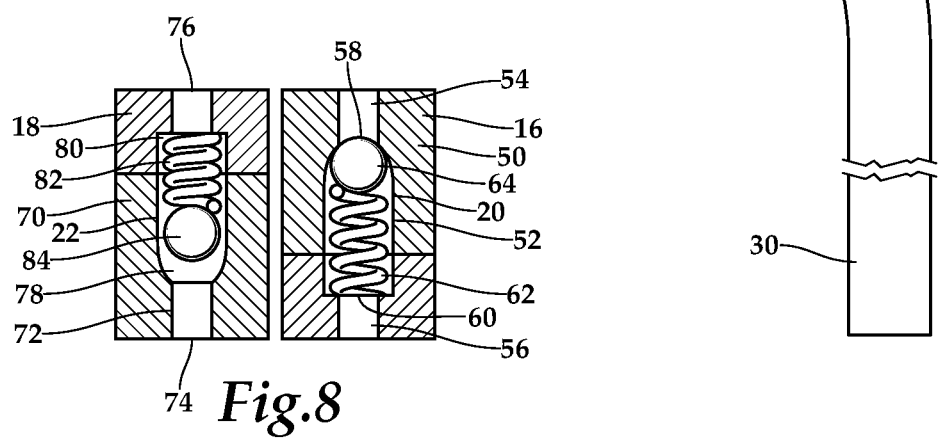

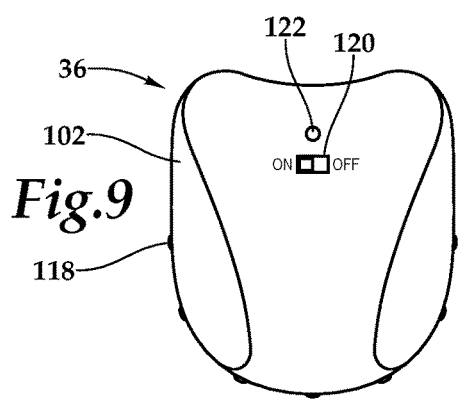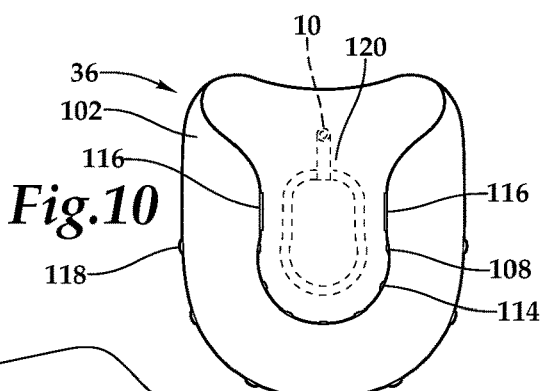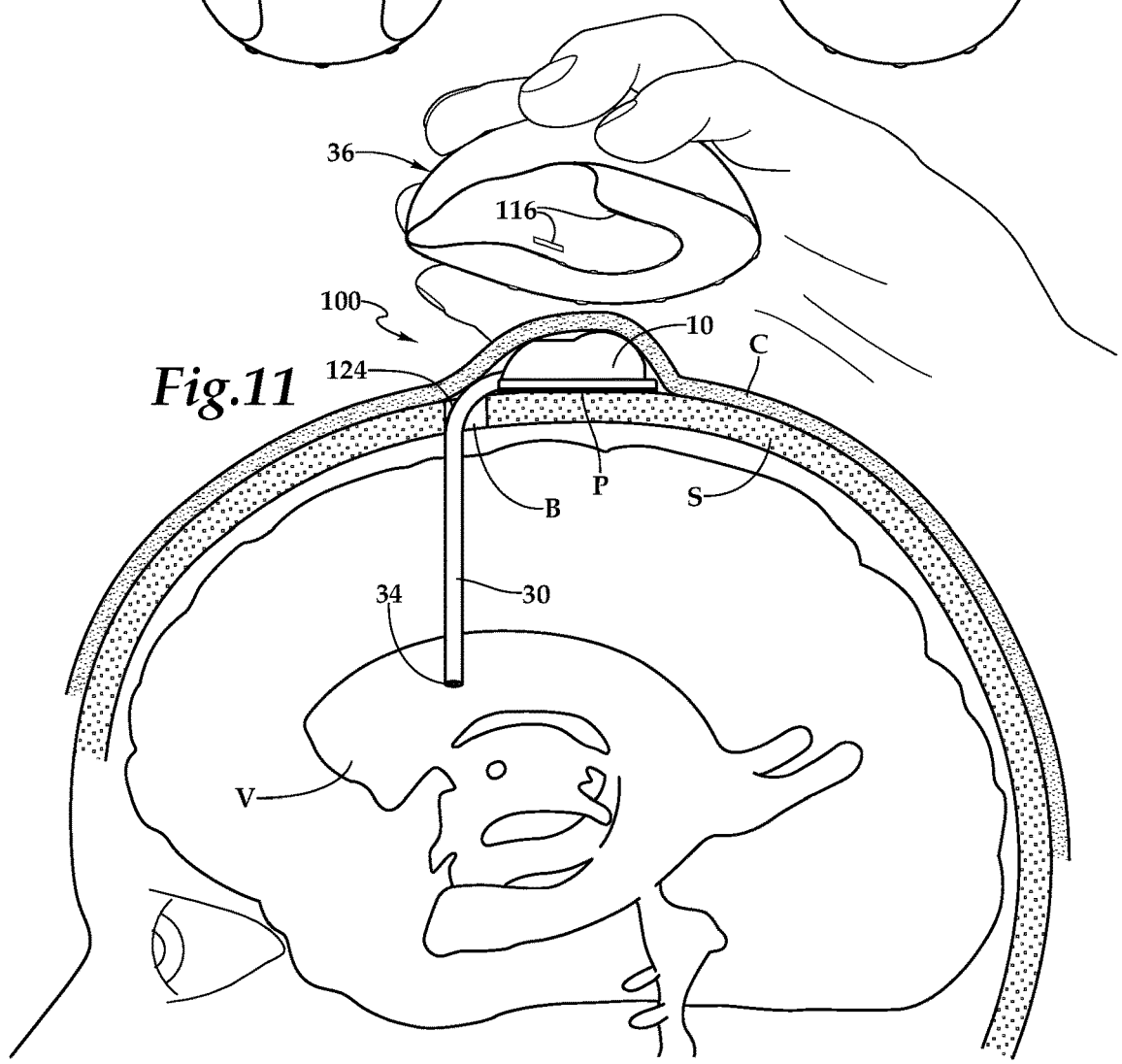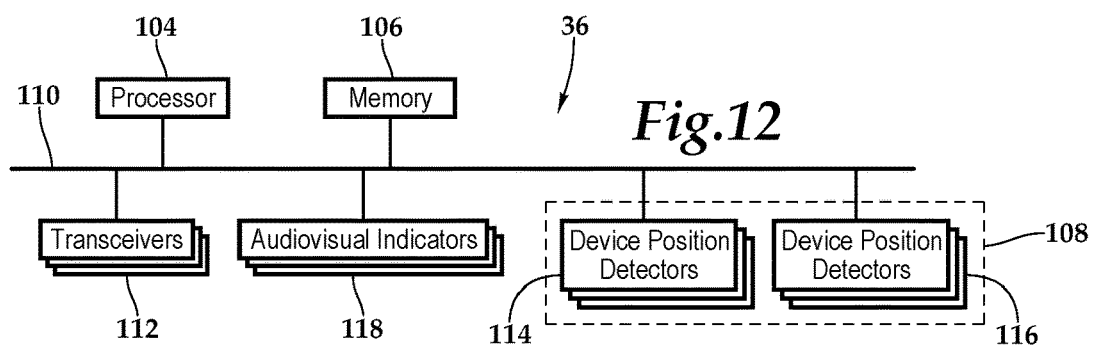

IMPLANTABLE INTRACRANIAL PULSE PRESSURE MODULATOR AND SYSTEM AND METHOD FOR USE OF SAME

PRIORITY STATEMENT & CROSS-REFERENCE TO RELATED APPLICATIONS

This application is a continuation of U.S. patent application Ser. No. 16/866,350 entitled "Implantable Intracranial Pulse Pressure Modulator and System and Method for Use of Same," filed on May 4, 2020, in the name of Frederick H. Sklar, now U.S. Pat. No. 11,103,683 issued on Aug. 31, 2021; which claims priority of U.S. Patent Application Ser. No. 62/972,617, entitled "Implantable Intracranial Pulse Pressure Modulator and System and Method for Use of Same," and filed on Feb. 10, 2020, in the name of Frederick H. Sklar; both of which are hereby incorporated by reference, in entirety, for all purposes.

TECHNICAL FIELD OF THE INVENTION

This invention relates, in general, to the treatment of hydrocephalus and, in particular, to an implantable surgical device, namely, an implantable intracranial pulse pressure modulator for treating hydrocephalus.

BACKGROUND OF THE INVENTION

Cerebrospinal fluid (CSF) is made within the cerebral ventricles by both active and passive processes. CSF percolates through the cerebral ventricular system, as well as the brain itself, and it is ultimately absorbed into intracranial and intraspinal veins, thereby establishing a so-called CSF circulation. It is generally taught that there must be a balance between how much CSF is made and absorbed, and hydrocephalus is said to result when absorption is reduced for some reason, such as the result of inflammation or subarachnoid hemorrhage. In addition, processes that physically deform the brain or obstruct the ventricular system can block CSF pathways and flow, such as seen with tumors, cysts, and various congenital malformations. Supposedly less CSF can be absorbed in these individuals because the circulation has been disturbed and hydrocephalus therefore develops. For the most part, rates of CSF formation are independent of intracranial pressure (ICP), although CSF production may diminish at very high ICP. In contrast, CSF absorption is a very sensitive function of ICP, increasing with increasing pressure over a threshold pressure even in patients with hydrocephalus, although perhaps not as efficiently as in normal individuals.

The ventriculoperitoneal shunt (VP shunt) was developed in the 1950s, and this represented a major milestone in modern neurological surgery, for it offered a fairly reliable and effective treatment for hydrocephalus in patients in which the hydrocephalus was not the result of an underlying disease process that could be treated some other way, such as excising the tumor causing CSF obstruction, etc. The VP shunt literally shunts (diverts) CSF from the cerebral ventricles to the peritoneal cavity, where it is absorbed into the venous system. Sometimes after multiple VP shunts and/or infections involving the peritoneal cavity, VP shunts are not successful because of peritoneal adhesions, loculations, or an inability for the diverted CSF to be resorbed. In those instances, CSF can be shunted from a cerebral ventricle into the pleural spaces around the lungs (V-pleural shunt), the right atrium of the heart (VA shunt), or the gall bladder (VGB shunt). These various ventricular shunts present their own set of risks and complications, and they are considered distant second choice procedures to the VP shunt.

Overall, patients generally do reasonably well with shunts, although the devices are associated with significant risks. To name only a few, shunts can break, obstruct, become infected, and erode into other organs. There are innumerable kinds of shunts in the marketplace, and shunt surgery (new shunts, revisions of shunts, and management of the complications) is said to have accounted for more than a billion dollars in year 2000 of American annual healthcare costs. There are programmable shunts, anti-siphoning shunts, shunts that can be pumped, shunts that can be tapped, shunts with anti-bacterial coatings, pressure differential shunts, flow regulated shunts, high pressure shunts, and low pressure shunts. Approximately thirty percent (30%) of shunts fail within the first year after placement. Headaches with shunts are common. Approximately thirty percent (30%) of children with shunts have headaches that are frequently related to over-shunting (excessive drainage of CSF). In adults, and particularly in the elderly, over-shunting can cause subdural hemorrhage (bleeding over the surface of the brain), and this can be life threatening. Many of the complications relate to where and how much fluid is drained. Modern neurosurgery has never quite established how much CSF should be allowed to drain and how best to accomplish this. Shunt infections can be particularly devastating to young infants and children, interfering with intellectual development.

In the 1970s, various researchers were able to create hydrocephalus by implanting small, pulsating balloons in the cerebral ventricles of lambs. The balloon pulsations were synchronized to augment the intraventricular pulse pressure (IVPP). Patients with VP shunts frequently have ventricular asymmetries, and the cerebral ventricle containing the shunt catheter tends to be the smaller one. IVPP has been noted to be reduced in the cerebral ventricle with the shunt catheter, compared to the cerebral ventricle on the other side. Ventriculosubgaleal shunts (VSG shunts) have been used for years as an effective alternative of a VP shunt in tiny premature infants who have developed hydrocephalus after intraventricular hemorrhage (IVH). Premature babies are at great risk of abdominal complications with the traditional preferred VP shunt procedure, and these problems are avoided with surgical procedures that can treat the hydrocephalus temporarily without involving the peritoneal cavity until these tiny infants are bigger and healthier. Accordingly, the placement of a reservoir to allow frequent removal of ventricular fluid or placement of a VSG shunt is frequently done with fair results. The VSG shunt option is interesting, because CSF is diverted into a subgaleal pocket created by the surgeon over the one-way-only shunt device.

In order to explain why this procedure is so effective in treating hydrocephalus, some neurosurgeons have suggested the excess CSF is actually resorbed by the galea—the undersurface of the scalp. More likely, however, the VSG shunt serves as a shock absorber, reducing the IVPP by allowing a small aliquot of CSF to leave the cerebral ventricle with every heartbeat therefore reducing the IVPP. In fact, this phenomenon is likely the actual mechanism of action of traditional ventricular shunts: the systolic pressure spike displaces a small CSF volume into the ventricular catheter, and it cannot return into the cerebral ventricle because of the presence of a one-way valve. This removal of a small volume of CSF reduces the systolic peak pressure, which reduces the IVPP and serves to treat the hydrocephalus. The actual draining of fluid into the peritoneal cavity, pleural space, or right atrium is an epiphenomenon and likely has nothing to do with the effective treatment of hydrocephalus. However, CSF drainage directly and indirectly has much to do with many of the complications that occur with frequency with ventricular shunt surgeries.

Existing implantable devices reduce the IVPP as a treatment of hydrocephalus. Such devices are designed to actively induce ventricular volume changes with an intrinsic pump controlled by a microprocessor and a rechargeable battery system. This approach serves to endorse the concept that pathologic augmentation of IVPP is indeed the underlying pathologic process in hydrocephalus, but the complexity of technology of this invention is somewhat worrisome as the first implantable device to treat hydrocephalus. Advances in medical science are needed to treat hydrocephalus by focusing on reducing IVPP with simple and safe technical methodology.

SUMMARY OF THE INVENTION

It would be advantageous to achieve an advanced, implantable device that can treat hydrocephalus without having to drain CSF from the cerebral ventricles to another body cavity. Moreover, it would be preferable if this device were designed for simplicity and to function passively, utilizing physiologic pressure changes that occur within the cerebral ventricles during the cardiac cycle, thereby not requiring complicated technical and electrical components. To better address one or more of these concerns, a surgically implantable passive intracranial pulse pressure modulator for treating hydrocephalus in patients of all ages is disclosed as well as a system and method for use of the same.

In one aspect, some embodiments of the implantable intracranial pulse pressure modulator include two one-way valves that are interposed in parallel, opposing orientations between a vestibule and a chamber. Each of the one-way valves may be a passive ball check valve. One of the one-way valves, in response to systole, provides fluid communication from the vestibule to the chamber such that a small aliquot of CSF is displaced from the cerebral ventricle into a ventricular catheter, thereby reducing the intraventricular systolic pressure. The other one-way valve, in response to diastole, provides fluid communication from the chamber to the vestibule such that the same volume of CSF is displaced from the vestibule and reintroduced into the cerebral ventricle, thereby increasing the intraventricular diastolic pressure. Together, both processes work synergistically to reduce IVPP in order to treat hydrocephalus.

In another aspect, some embodiments are directed to a system for treating hydrocephalus. An implantable intracranial pulse pressure modulator includes a housing sized for superjacent contact with a skull. The housing secures a vestibule, two one-way valves, and a chamber therein. The housing includes fine metallic particles impregnated therein. The vestibule has a receiving member configured to couple to an intraventricular catheter. The two one-way valves are interposed in parallel with opposing orientations between the vestibule and the chamber. One of the one-way valves, in response to systole, provides fluid communication from the vestibule to the chamber. The second one-way valve, in response to diastole, provides fluid communication from the chamber to the vestibule. Fluid flows from the vestibule to the chamber during the latter part of systole, when the intraventricular pressure exceeds the pressure in the chamber. Fluid flows from the chamber to the vestibule during the early part of diastole, when the pressure in the chamber is greater than the pressure in the vestibule.

In some embodiments, an accessory device may include a housing securing a processor, memory, and a plurality of position detectors therein. A busing architecture communicatively interconnects the processor, the memory, and the position detectors. The position detectors are configured to detect the position of the implantable intracranial pulse pressure modulator and the position of the two one-way valves. In other embodiments, the accessory device is an ultrasound probe that detects the position of the two one-way valves. These and other aspects of the invention will be apparent from and elucidated with reference to the embodiments described hereinafter.

BRIEF DESCRIPTION OF THE DRAWINGS

For a more complete understanding of the features and advantages of the present invention, reference is now made to the detailed description of the invention along with the accompanying figures in which corresponding numerals in the different figures refer to corresponding parts and in which:

FIG. 1 is a top perspective view of one embodiment of an implantable intracranial pulse pressure modulator, according to the teachings presented herein;

FIG. 2 is a front elevation view of the implantable intracranial pulse pressure modulator depicted in FIG. 1;

FIG. 3 is a rear elevation view of the implantable intracranial pulse pressure modulator depicted in FIG. 1;

FIG. 6 is a left elevation view of the implantable intracranial pulse pressure modulator depicted in FIG. 1;

FIG. 7 is a right elevation view of the implantable intracranial pulse pressure modulator depicted in FIG. 1;

FIG. 8 is a top plan view of a pair of one-way valves, which form a portion of the implantable intracranial pulse pressure modulator depicted in FIG. 1;

FIG. 9 is a top plan view of an accessory device of the implantable intracranial pulse pressure modulator;

FIG. 10 is a bottom plan view of the accessory device depicted in FIG. 9;

FIG. 11 is a schematic illustration of one embodiment of a system for treating hydrocephalus, according to the teachings presented herein;

FIG. 12 is a functional block diagram of one embodiment of the accessory device depicted in FIG. 9;

DETAILED DESCRIPTION OF THE INVENTION

Figure 4:
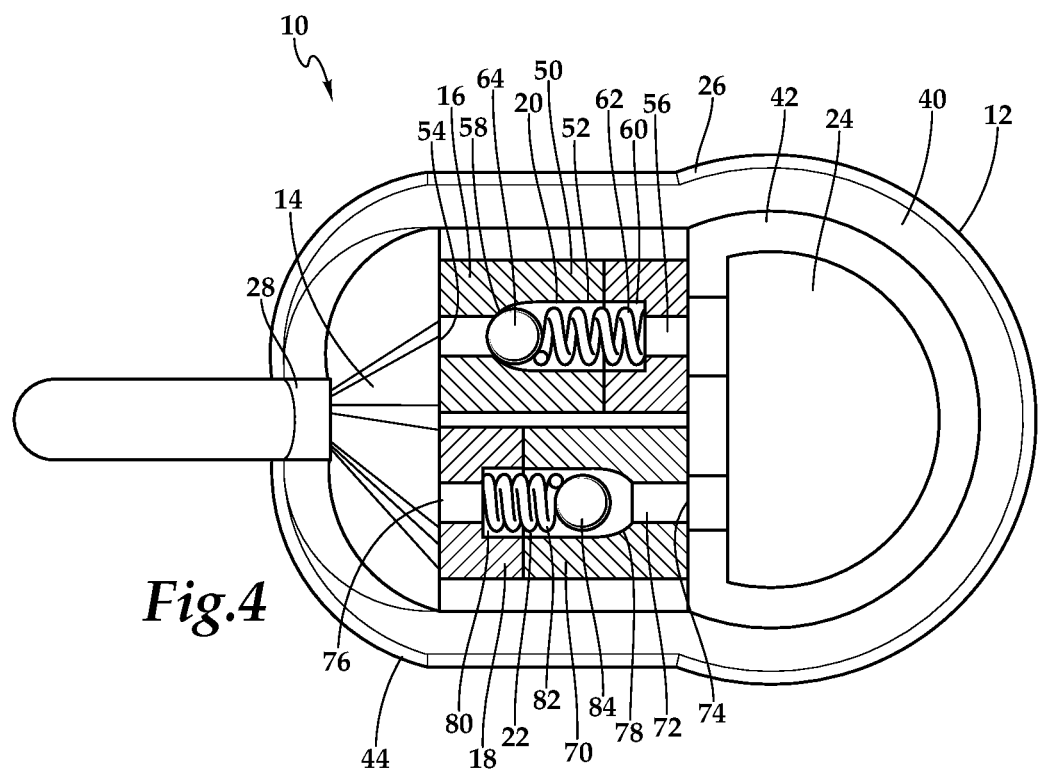
FIG. 4 is a top plan view of the implantable intracranial pulse pressure modulator depicted in FIG. 1.
Figure 5:
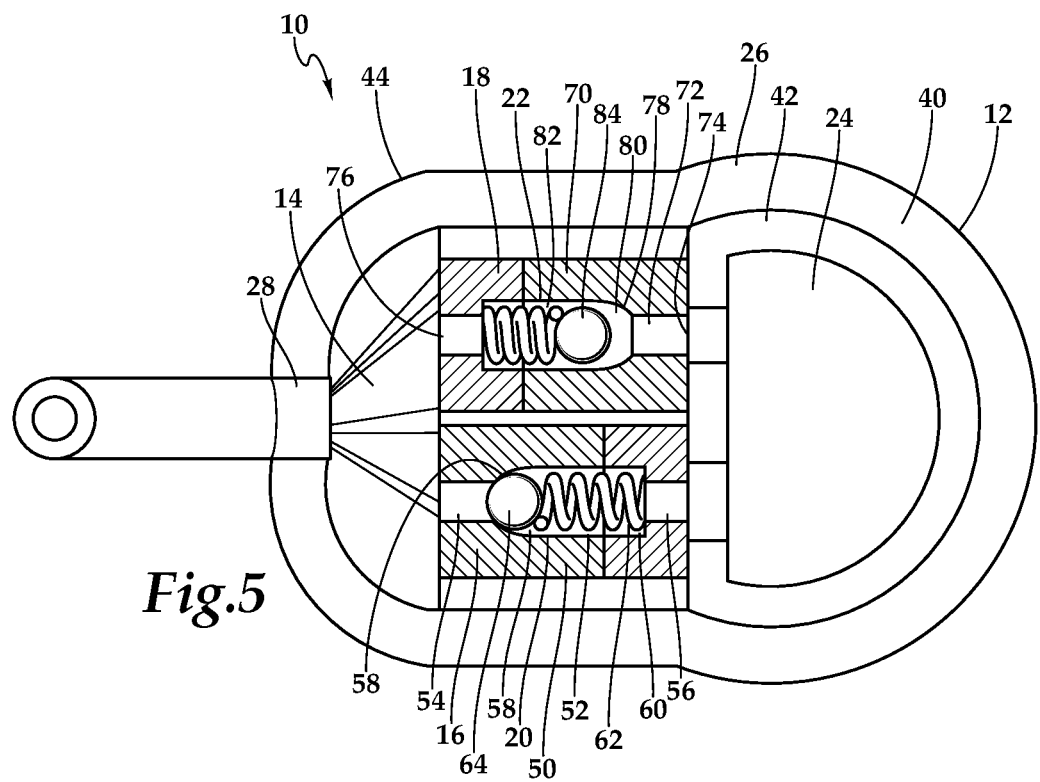
FIG. 5 is a bottom plan view of the implantable intracranial pulse pressure modulator depicted in FIG. 1.

While the making and using of various embodiments of the present invention are discussed in detail below, it should be appreciated that the present invention provides many applicable inventive concepts which can be embodied in a wide variety of specific contexts. The specific embodiments discussed herein are merely illustrative of specific ways to make and use the invention and do not delimit the scope of the present invention.

Referring initially to FIG. 1 through FIG. 8, therein is depicted one embodiment of an implantable intracranial pulse pressure modulator device (IPPMD) that is schematically illustrated and generally designated 10. As shown, a housing 12 is sized for superjacent contact with a skull S. The housing 12 secures a vestibule 14, a pair of one-way valves 16, 18 exemplarily depicted as passive ball check valves 20, 22, and a chamber 24 therein. Walls of the chamber 24 may be comprised of an elastic material such as silicone that allows the volume of the chamber 24 to change slightly. The base 40 of the housing 12 may include fine metallic particles 26 impregnated therein, or the housing 12 may include another material that may be identified by position detection or ultrasound, for example. Such particles may be impregnated within the perimeter rim 44. The vestibule 14 has a receiving member 28 configured to couple to an intraventricular catheter 30, which forms the intracranial component of the IPPMD 10. The intraventricular catheter 30 may be constructed of silicone or other appropriate polymer that provides a radio-opaque appearance on x-rays and scans. Additionally, the intraventricular catheter 30 may include markings, such as centimeter markings 32, to facilitate its placement into a cerebral ventricle V. The intraventricular catheter 30 has an end 34 (best seen in FIG. 11) and in one embodiment, the end 34 may include an open tip. In another embodiment, the end 34 may include a blunt, closed tip with multiple small holes positioned around the circumference of the intraventricular catheter 30 for an initial length, such as one centimeter. It should be appreciated that it is not anticipated that the intraventricular catheter 30 will be subject to obstruction by the choroid plexus and ependymal tissue to the marked degree as are existing ventricular catheters in present use with traditional shunts.

The housing 12 includes a base 40 and a body 42. The base 40 may include a circumferential rim 44 that provides an interface for sutures to be placed. In this manner, the IPPMD 10 may be secured to the pericranium P (best seen in FIG. 11), a fibrous membrane that is adherent to the outer surface of the skull S (best seen in FIG. 11). In one embodiment, the circumferential rim 44 is 2 mm wide and 2 mm thick. The upper 1 mm thickness of this circumferential rim (i.e., the dorsal surface of the circumferential rim 44), may be comprised of silicone impregnated with the fine metallic particles 26, or other appropriate material. Accordingly, with the impregnated fine metallic particles 26, as will be discussed in FIG. 9 through FIG. 11, the position of the base 40 of the housing 12 may be detected by capacitive position sensors arranged in the floor of an accessory device 36.

The one-way valves 16, 18 are interposed in parallel between the vestibule 14 and the chamber 24. Moreover, the one-way valves 16, 18 are positioned with opposing orientations. In the illustrated embodiment, the housing 12 includes a valve box 46, which has the two one-way valves 16, 18 therein. The valve box 46 may include a silicone-based construction. As previously discussed, in one embodiment, the one-way valve 16 is the passive ball check valve 20 and the one-way valve 18 is the passive ball check valve 22. Other kinds of one-way valves may be utilized such as miniature passive check valves, flap valves, membrane valves, cantilever valves, or Tesla valves. However, using passive ball check valves provides metal ball valves and springs that furnish the added advantage of being able to monitor transcutaneously the reciprocal movements of the balls with the external micro movement sensors of a tester, such as the accessory device 36, as a test to determine whether or not the IPPMD 10 is functioning correctly. It should be appreciated that other features may be present with the IPPMD 10. By way of example, and not by way of limitation, the chamber 24 may be a tap chamber configured to accept a needle.

In operation, the one-way valve 16, in response to systole, provides fluid communication from the vestibule 14 to the chamber 24. In response to diastole, the one-way valve 16 blocks fluid communication between the vestibule 14 and the chamber 24. On the other hand, the one-way valve 18, in response to diastole, provides fluid communication from the chamber 24 to the vestibule 14. In response to systole, the one-way valve 18 blocks fluid communication between the vestibule 14 and the chamber 24. More particularly, fluid flows from the vestibule 14 to the chamber 24 during the latter part of systole, when the intraventricular pressure surpasses the pressure in the chamber 24, and fluid flows from the chamber 24 to the vestibule 14 during the early part of diastole, when the pressure in the chamber 24 is greater than the pressure in the vestibule 14.

As mentioned, the one-way valve 16 may be the passive ball check valve 20 and the one-way valve 18 may be the passive ball check valve 22. In some embodiments, the passive ball check valve 20 may include a body 50 having a channel 52 with an inlet 54 and outlet 56 therethrough. The inlet 54 may be proximate the vestibule 14 and the outlet 56 may be proximate the chamber 24. A seat 58 intersects the body 50 proximate the inlet 54. A mounting member 60 secures a spring 62 to the body 50 proximate the outlet 56. A ball 64 is coupled to the spring 62 opposite the mounting member 60 with the spring 62 biasing the ball 64 into contact with the seat 58. It should be appreciated that the spring 62 may be positioned within the channel 52 proximate the outlet 56 and the ball 64 interposed between the spring 62 and the seat 58. In this manner, the spring 62, the ball 64, or the spring 62 and the ball 64 may be floating. The ball 64, in response to a minimum inlet-to-outlet pressure, is displaced from the seat 58 to provide for fluid communication through the channel 52 from the inlet 54 to the outlet 56. The passive ball check valve 20 may include a cracking pressure equal to an intraventricular pulse pressure that displaces an aliquot of cerebrospinal fluid. The cracking pressure may be a differential pressure between zero and the untreated intraventricular pulse pressure that allows for displacement of an aliquot of cerebrospinal fluid.

In operation, the passive ball check valve 20, in response to diastole, blocks fluid communication between the vestibule 14 and the chamber 24. The passive ball check valve 20, in response to systole, provides fluid communication from the vestibule 14 to the chamber 24 upon an aliquot of cerebrospinal fluid from a cerebral ventricle V (see FIG. 11) entering the intraventricular catheter 30 and increasing pressure in the vestibule 14.

The passive ball check valve 22 may be similar to the passive ball check valve 20. In one implementation, with respect to the passive ball check valve 22, a body 70 includes a channel 72 having an inlet 74 and an outlet 76 therethrough with the inlet 74 being proximate the chamber 24 and the outlet 76 proximate the vestibule 14. A seat 78 intersects the body 70 proximate the inlet 74 and a mounting member 80 secures a spring 82 to the body 70 proximate the outlet 76. A ball 84 is coupled to the spring 82 opposite the mounting member 80 such that the spring 82 biases the ball 84 into contact with the seat 78. It should be appreciated that the spring 82 may be positioned within the channel 72 proximate the outlet 76 and the ball 84 interposed between the spring 82 and the seat 78. In this manner, the spring 82, the ball 84, or the spring 82 and the ball 84 may be floating. The spring 82, in response to a minimum inlet-to-outlet pressure, is displaced from the seat 78 to provide for fluid communication through the channel 72 from the inlet 74 to the outlet 76. The passive ball check valve 22 may have a cracking pressure equal to an intraventricular pulse pressure that displaces an aliquot of cerebrospinal fluid. Moreover, the cracking pressure may be between the peak systolic pressure and minimum diastolic pressure.

In operation, the passive ball check valve 22, in response to systole, blocks fluid communication between the tap chamber 24 and the vestibule 14. The passive ball check valve 22, in response to diastole, provides fluid communication from the chamber 24 to the vestibule 14 upon an aliquot of cerebrospinal fluid from the intraventricular catheter 30 entering the cerebral ventricle V and decreasing a pressure in the vestibule 14.

During systole, the IPPMD 10 allows only a small volume of CSF to enter the end 34 of the intraventricular catheter 30 and during diastole, another small volume of CSF (probably of equal volume) is pushed back into the cerebral ventricle V. In contrast, in traditional ventricular shunts, a small volume of CSF enters the shunt catheter in systole. However, in diastole, if the shunt is not siphoning (a problem that exists with most traditional shunts), CSF does not move in the reverse direction in the ventricular catheter because the shunts have a one-way valve. Unlike the IPPMD 10, no fluid is reintroduced into the cerebral ventricle V during diastole, and a staccato-like current of CSF is established in the ventricular catheter in a direction away from the cerebral ventricle V. Moreover, if the weight of the water in the peritoneal catheter of the traditional ventricular shunt can exert a negative pressure enough to overcome the opening pressure of the valve, CSF will flow away from the cerebral ventricle V, not only in systole, but also in diastole. In both situations, choroidal and ependymal tissue are sucked into the opening(s) of the ventricular catheter. Eventually, the ventricular catheter of traditional shunts may become obstructed. In fact, so-called "proximal shunt obstruction" (occlusion of the ventricular catheter) is the most common significant complication of traditional ventricular shunts. In contrast, there is no CSF current established within the ventricular catheter of the IPPMD 10, since the net directional flow of CSF over the entire cardiac cycle is zero. If the IPPMD 10 indeed has a significant lower risk/incidence of "proximal shunt obstruction," this would be a remarkable advantage of this new device over traditional shunts.

Referring now to FIG. 9 through FIG. 12, in some embodiments, in a system 100, the accessory device 36 includes a housing 102 securing a processor 104, memory 106, and position detectors 108 therein. The housing 102 of the accessory device 36 may be sized for hand-held operation. A busing architecture 110 communicatively interconnects the processor 104, the memory 106, and the capacitive position detectors 108. One or more wireless transceivers 112 may be associated with the housing 102 and coupled to the busing architecture 110. The wireless transceivers 112 may be configured to communicate with a computing device via a wireless protocol. The processor 104 may process instructions for execution within the accessory device 36 as a computing device, including instructions stored in the memory 106. The memory 106 stores information within the computing device. In one implementation, the memory 106 may be a volatile memory unit or units, a non-volatile memory unit or units, capacity that is capable of providing mass storage, or a combination thereof. Further, the processor 104 and the memory 106 may be embodied as a microcontroller or a microprocessor.

The position detectors 108 may include device position detectors 114 that are configured to detect the position of the accessory device 36 with respect to the IPPMD 10. The position detectors 108 may also include valve position detectors 116 that are configured to detect the position of the one-way valve 16 and the one-way valve 18. That is, the position detectors 108 are configured to detect the alignment of the accessory device 36 over the IPPMD 10 and, responsive to correct positioning, track the movement of the stainless steel balls, or balls of another suitable composition, within the one-way valves 16, 18. Audiovisual indicators 118, which provide data to the user, are associated with the housing 102 and coupled to the busing architecture 110. The audiovisual indicators 118 may include audio signals, visuals signals, or a combination thereof.

The accessory device 36 may be a handheld accessory device that, in one embodiment, is shaped to be comfortable in a cupped hand of the care provider. The bottom of the accessory device 36 may have a concave contour to accept the prominence of the dorsal surface of the IPPMD 10 under the patient's scalp. As mentioned, the device position detectors 114 may include multiple capacitive position sensors that are arranged within the accessory device 36 in an array that mirrors the circumferential rim 44 of the housing 12. Also in the accessory device 36 is the aforementioned circuitry, e.g., the processor 104 and the memory 106 that monitor the positioning of the accessory device 36, once it has been placed over the IPPMD 10 and a power switch 120, for example, has been turned ON. The accessory device 36 may record the electrical signal from each position detector 108 and cause a colored LED 122, part of the audiovisual indicators 118, to signal on the dorsal surface of the accessory device 36 as an indication that the accessory device 36 is over the circumferential rim 44 of the housing 12 with a green light, as opposed to not being over the circumferential rim 44 with a red light. On the dorsal surface of the accessory device 36, the audiovisual indicators 118, which may also be LED lights, are arranged in two concentric shapes that mimic the circumferential rim 44 of the housing 12. The care provider carefully adjusts the position of the accessory device 36 so that all of the audiovisual indicators 118 are green. Once all of the appropriate position detectors 108 are over the housing 12, the processor 104 turns on an orange (or other color) central visual LED light, which is part of the audiovisual indicators 118, apparent to the care provider, to indicate that approximately ten (10) or more, for example, cardiac cycles are being examined by tracking the reciprocal movements of the balls 64, 84 with the valve position detectors 116, which may be two micro motion detectors, arranged within the accessory device 36, so that the valve position detectors 116 are in the sagittal plane of its respective passive ball check valve 20, 22, and it is facing the seat 58 or 78 of its respective passive ball check valve 20, 22. It should be appreciated that plastic springs may be available, if the metal springs interfere with position monitoring of the balls 64, 84, which may be stainless steel, of the passive ball check valves 20, 22.

Figure 13:
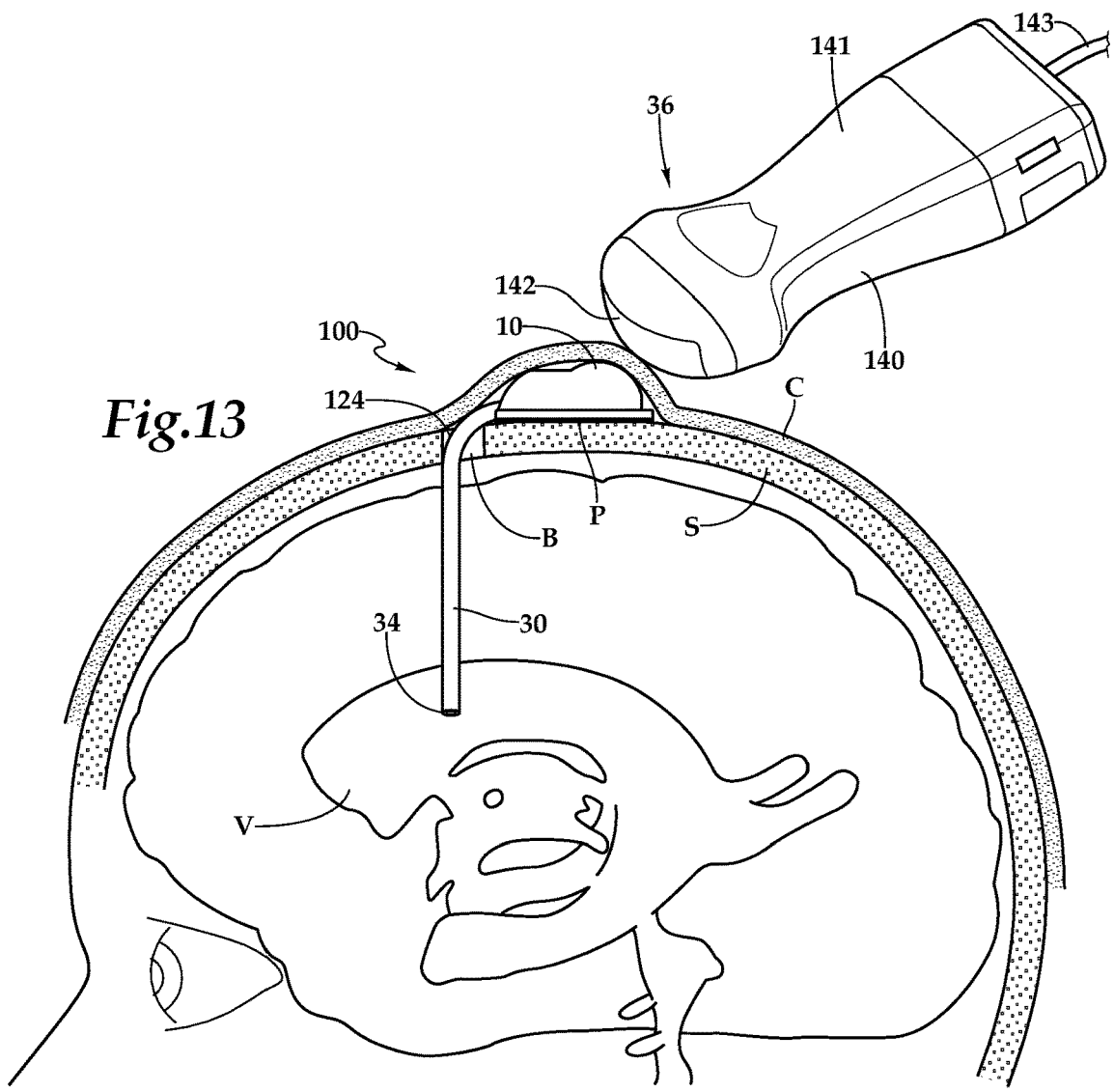
FIG. 13 is a schematic illustration of another embodiment of a system for treating hydrocephalus, according to the teachings presented herein.
Figure 14:
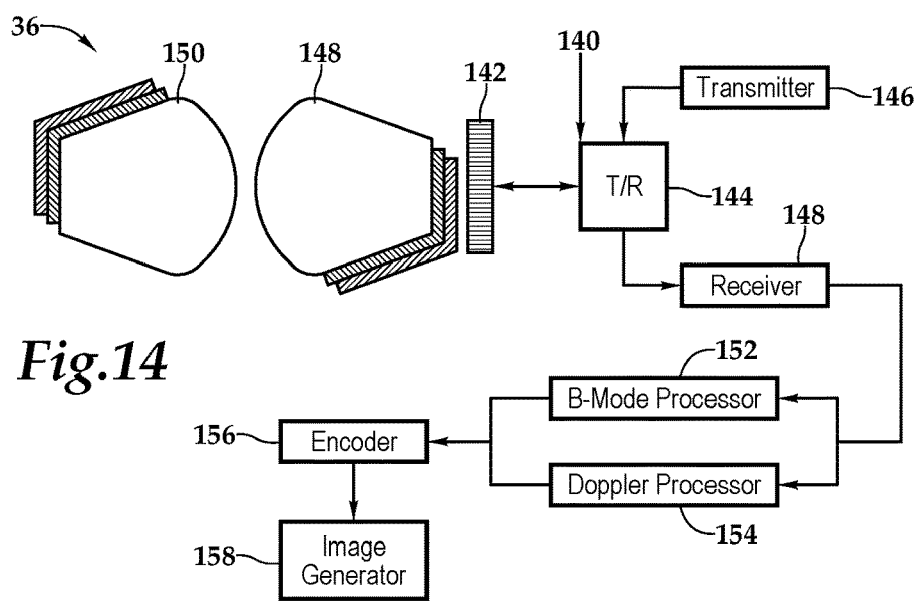
FIG. 14 is a functional block diagram of another embodiment of an accessory device.

In another embodiment, with reference to FIG. 13 and FIG. 14, ultrasound may be an equally effective method to detect and quantify movement of the balls 64, 84 in the passive ball check valves 20, 22, since stainless steel will be opaque with this technique, which may prove advantageous to block out distracting echoes from behind the balls 64, 84. On the other hand, echogenic artifact from the metal balls 64, 84 may be avoided with other ball materials such as glass, sapphire, ruby, and diamonds. All of these materials are commercially available as check valve balls and are durable alternatives to stainless steel balls. With ultrasound, the care provider may move the accessory device, which is an ultrasound probe 140, which may be handheld with a housing 141 and cabling 143, over the IPPMD 10 to locate the passive ball check valves 20, 22 and orient the handheld probe appropriately to define best the extent of the cyclical, reciprocal movements of the balls 64, 84. With respect to the accessory device 36 having ultrasound capabilities, the ultrasound probe 140 is configured to track the movement of the one-way valves 16, 18. More particularly, a transducer probe 142 is coupled to a switch 144 which, in turn, is connected to a transmitter 146 and a receiver 148. When actuated by the switch 144, the transmitter 146 applies transducer waveforms to the transducer probe 142, thereby causing the transducer probe 142 to emit beams of ultrasonic energy 148 directed along selected scan lines. Returning echoes 150 are received from the balls 64, 84 in the passive ball check valves 20, 22 being impinged upon. When actuated by the switch 144, the receiver 148 processes the returning echoes 150 via a B-mode processor 152 and a Doppler processor 154. The B-mode processor 152 produces output signals indicative of an intensity of the returning echoes 150 and the Doppler processor 154 produces output signals indicative of a Doppler parameter such as Doppler velocity or Doppler energy along the selected scan lines. The output signals from the B-mode processor 152 and the Doppler processor 154 are applied to an encoder 156 that generates composite data which is transformed into an image by an image generator 158. It should be appreciated that although a particular ultrasound probe 140 is presented herein, other types of ultrasound probes are within the teachings of the present invention presented herein.

Moreover, regardless of the embodiment, the accessory device 36, and, in particular, the accessory device of FIG. 9 through FIG. 12, may have wireless capabilities, such as Bluetooth capabilities, so that the measurement data can be transferred to a nearby computer for sophisticated evaluation and documentation. In this way, the care provider will be provided information about whether the passive ball check valves 20, 22 are opening and closing relative to the cardiac cycle, and whether one or both show limited or no movement that may indicate malfunction of the IPPMD 10.

The IPPMD 10 may include both intracranial and extracranial components. The intracranial component is the intraventricular catheter 30, a radio-opaque silicone catheter, which would be introduced through a burr hole B in the skull S into a cerebral ventricle V from any of the standard ventricular shunt locations. The proximal end of the intraventricular catheter 30 may have a 90° turn at 124 as it exits the skull S and connects to the extracranial component of the IPPMD 10. In some embodiments, this extracranial component consists entirely of the housing 12, which may be made of silicone and has a small (2×3 cm) footprint and a profile with a maximal height of 1 cm. It should be appreciated, however, that the form factor and size may vary depending on the application.

During cardiac systole, the pressure in the cerebral ventricle V increases higher than the pressure in the intraventricular catheter 30, causing an aliquot of CSF to move into the catheter. This, in turn, causes all of the respective CSF aliquots above the first one (just inside the catheter tip) to move toward the vestibule 14 and the vestibular ends of the two passive ball check valves 20, 22. A pressure gradient develops during systole so that the pressure in the vestibule 14 surpasses that of the chamber 24, and CSF flows across the passive ball check valve 20 into the chamber 24 as long as the passive ball check valve 20 remains open. As the cardiac cycle progresses into diastole, the pressure in the cerebral ventricle drops below the pressure in the chamber 24, which closes the passive ball check valve 20 and opens the second passive ball check valve 22, thereby allowing CSF to move back into the cerebral ventricle V during diastole. To summarize, the peak systolic pressure is initially reduced by the flow of an aliquot of CSF from the cerebral ventricle V into the IPPMD 10. In diastole, a CSF aliquot flows back into the cerebral ventricle V, thereby raising the diastolic pressure, which reduces the pulse pressure (PP) yet again. This can be appreciated mathematically with the following:

$$PP = \text{peak systolic pressure} - \text{lowest diastolic pressure}$$

Accordingly, PP is decreased twice with every cardiac cycle. Initially in systole, it is decreased by reducing the peak systolic pressure; and in diastole, by increasing the lowest diastolic pressure. Both mechanisms collectively serve to decrease PP. The mean intraventricular pressure is the same with or without the device. In contrast, traditional ventricular shunts reduce only the systolic pressure and do not affect the diastolic pressure, unless the shunt is siphoning. With siphoning, the diastolic pressure would decrease, thereby increasing PP—an undesirable effect. By decreasing the IVPP, the IPPMD 10 may more effectively treat hydrocephalus, as compared to both non-siphoning and siphoning traditional VP shunts. Moreover, this IPPMD 10 does not depend on complicated electronic micro pumps, microcontrollers, balloons, transmitters, or other technology to achieve pulse pressure reductions. In contrast, in some embodiments, the IPPMD 10 has only four moving parts within the passive ball check valves 20, 22, balls 64, 84, and two springs 62, 82, which function passively, driven by the intraventricular pressure (IVP) changes induced by the heart during the cardiac cycle. The IPPMD 10 can be made smaller without much effort.

Moreover, clinical functioning of the IPPMD 10 can be assessed with the accessory device 36, a tester that tracks the reciprocal movements of the balls 64, 84 and springs 62, 82. A shunt tap can be performed by introducing a small gauge needle into the chamber 24 in order to measure pressure and aspirate CSF for laboratory analysis and culture.

The length of the intraventricular catheter 30 deserves comment. One embodiment is to provide the IPPMD 10 with a single, long intraventricular catheter 30 with a single end opening, and the surgeon can cut it to the correct length according to the patient's anatomy. Other embodiments may offer the IPPMD 10 with various lengths of intraventricular catheter 30, and the surgeon can pick the best one for the job. The disadvantage of the former embodiment is that the surgeon may not make a clean cut of the intraventricular catheter 30, and the tip of the intraventricular catheter 30 may have a ragged, or even sharp edge (if the cut is not perpendicular to the axis of the tube). One solution is to provide a simple, plastic cutter tool with a slot for the intraventricular catheter 30 to be cut by a guillotine-like blade (or another device that insures a clean, perpendicular cut) with each IPPMD 10 manufactured with long catheters for the surgeon to trim to size. Furthermore, it is suggested that the ventricular catheter be manufactured as a contiguous component of the IPPMD 10 to avoid assembling of the ventricular catheter 30 to the housing 12 by the surgeon during surgery, thereby eliminating a connection site that commonly breaks.

The order of execution or performance of the methods and process flows illustrated and described herein is not essential, unless otherwise specified. That is, elements of the methods and process flows may be performed in any order, unless otherwise specified, and that the methods may include more or less elements than those disclosed herein. For example, it is contemplated that executing or performing a particular element before, contemporaneously with, or after another element are all possible sequences of execution.

While this invention has been described with reference to illustrative embodiments, this description is not intended to be construed in a limiting sense. Various modifications and combinations of the illustrative embodiments as well as other embodiments of the invention, will be apparent to persons skilled in the art upon reference to the description. It is, therefore, intended that the appended claims encompass any such modifications or embodiments.

What is claimed is:

1. An implantable intracranial pulse pressure modulator for treating hydrocephalus, the implantable intracranial pulse pressure modulator comprising:
   a shuntless housing sized for superjacent contact with a skull, the shuntless housing securing a vestibule, first and second passive ball check valves, and a chamber therein, the vestibule, first and second passive ball check valves, and the chamber, in combination, providing zero net flow of cerebrospinal fluid;
   the vestibule having a receiving member configured to couple to an intraventricular catheter;
   the first and second passive ball check valves being interposed in parallel between the vestibule and the chamber, the first and second passive ball check valves being positioned with opposing orientations;
   the first passive ball check valve, in response to systole, providing fluid communication from the vestibule to the chamber upon an aliquot of cerebrospinal fluid from a cerebral ventricle entering the intraventricular catheter and increasing a pressure in the vestibule; and
   the second passive ball check valve, in response to the reduction of intraventricular pressure during diastole, providing fluid communication from the chamber to the vestibule upon an aliquot of cerebrospinal fluid from the intraventricular catheter entering a cerebral ventricle and decreasing a pressure in the vestibule.

2. The implantable intracranial pulse pressure modulator as recited in claim 1, wherein the shuntless housing further comprises a valve box, the valve box housing the first passive ball check valve and the second passive ball check valve therein.

3. The implantable intracranial pulse pressure modulator as recited in claim 1, wherein the first passive ball check valve further comprises:
   a body including a channel having an inlet and an outlet therethrough, the inlet being proximate the vestibule and the outlet being proximate the chamber;
   a seat intersecting the body proximate the inlet;
   a spring positioned within the channel proximate the outlet;
   a ball interposed between the spring and the seat;
   the spring biasing the ball into contact with the seat;
   the spring, in response to a minimum inlet-to-outlet pressure, being displaced from the seat to provide for fluid communication through the channel from the inlet to the outlet.

4. The implantable intracranial pulse pressure modulator as recited in claim 1, wherein the first passive ball check valve further comprises a cracking pressure equal to an intraventricular pulse pressure that displaces an aliquot of cerebrospinal fluid.

5. The implantable intracranial pulse pressure modulator as recited in claim 1, wherein the first passive ball check valve further comprises a cracking pressure between a peak intraventricular systolic pressure and a minimum intraventricular diastolic pressure.

6. The implantable intracranial pulse pressure modulator as recited in claim 1, wherein the second passive ball check valve further comprises:
   a body including a channel having an inlet and an outlet therethrough, the inlet being proximate the chamber and the outlet proximate the vestibule;
   a seat intersecting the body proximate the inlet;
   a spring positioned within the channel proximate the outlet;
   a ball interposed between the spring and the seat;
   the spring biasing the ball into contact with the seat;
   the spring, in response to a minimum inlet-to-outlet pressure, being displaced from the seat to provide for fluid communication through the channel from the inlet to the outlet.

7. The implantable intracranial pulse pressure modulator as recited in claim 1, wherein the second passive ball check valve further comprises a cracking pressure equal to an intraventricular pulse pressure that displaces an aliquot of cerebrospinal fluid.

8. The implantable intracranial pulse pressure modulator as recited in claim 1, wherein the first passive ball check valve, in response to diastole, blocks fluid communication between the vestibule and the chamber.

9. The implantable intracranial pulse pressure modulator as recited in claim 1, wherein the second passive ball check valve, in response to systole, blocks fluid communication between the chamber and the vestibule.

10. The implantable intracranial pulse pressure modulator as recited in claim 1, wherein the shuntless housing further comprises fine metallic particles impregnated therein.

11. The implantable intracranial pulse pressure modulator as recited in claim 1, wherein the chamber further comprises a tap chamber configured to accept a needle.

12. An implantable intracranial pulse pressure modulator for treating hydrocephalus, the implantable intracranial pulse pressure modulator comprising:
   a shuntless housing sized for superjacent contact with a skull, the housing securing a vestibule, first and second one-way valves, and a chamber therein, the vestibule, first and second one-way valves, and the chamber, in combination, providing zero net flow of cerebrospinal fluid;
   the vestibule having a receiving member configured to couple to an intraventricular catheter;
   the first and second one-way valves being interposed in parallel between the vestibule and the chamber, the first and second one-way valves being positioned with opposing orientations;
   the first one-way valve, in response to systole, providing fluid communication from the vestibule to the chamber upon an aliquot of cerebrospinal fluid from a cerebral ventricle entering the intraventricular catheter and increasing a pressure in the vestibule; and
   the second one-way valve, in response to a reduction of intraventricular pressure during diastole, providing fluid communication from the chamber to the vestibule upon an aliquot of cerebrospinal fluid from the intraventricular catheter entering a cerebral ventricle and decreasing a pressure in the vestibule.

13. The implantable intracranial pulse pressure modulator as recited in claim 12, wherein the first one-way valve further comprises a cracking pressure equal to an intraventricular pulse pressure that displaces an aliquot of cerebrospinal fluid.

14. The implantable intracranial pulse pressure modulator as recited in claim 12, wherein the first one-way valve further comprises a cracking pressure between a peak intraventricular systolic pressure and a minimum intraventricular diastolic pressure.

15. The implantable intracranial pulse pressure modulator as recited in claim 12, wherein the second one-way valve further comprises a cracking pressure equal to an intraventricular pulse pressure that displaces an aliquot of cerebrospinal fluid.

16. The implantable intracranial pulse pressure modulator as recited in claim 12, wherein the first one-way valve, in response to diastole, blocks fluid communication between the vestibule and the chamber.

17. The implantable intracranial pulse pressure modulator as recited in claim 12, wherein the second one-way valve, in response to systole, blocks fluid communication between the chamber and the vestibule.

18. The implantable intracranial pulse pressure modulator as recited in claim 12, wherein the shuntless housing further comprises fine metallic particles impregnated therein.

19. The implantable intracranial pulse pressure modulator as recited in claim 12, wherein the chamber further comprises a tap chamber configured to accept a needle.

20. An implantable intracranial pulse pressure modulator for treating hydrocephalus, the implantable intracranial pulse pressure modulator comprising:
- a shuntless housing sized for superjacent contact with a skull, the housing securing a vestibule, first and second valves, and a chamber therein, the vestibule, first and second valves, and the chamber, in combination, providing zero net flow of cerebrospinal fluid;
- the vestibule having a receiving member configured to couple to an intraventricular catheter;
- the first and second valves being interposed in parallel between the vestibule and the chamber, the first and second valves being positioned with opposing orientations;
- the first valve, in response to systole, including means for fluid communication from the vestibule to the chamber upon an aliquot of cerebrospinal fluid from a cerebral ventricle entering the intraventricular catheter and increasing a pressure in the vestibule; and
- the second valve, in response to a reduction of intraventricular pressure during diastole, including means for fluid communication from the chamber to the vestibule upon an aliquot of cerebrospinal fluid from the intraventricular catheter entering a cerebral ventricle and decreasing a pressure in the vestibule.

* * * * *